United States Patent [19]

Teare et al.

[11] Patent Number: 5,448,999
[45] Date of Patent: Sep. 12, 1995

[54] PROSTHETICS ELECTRODE ARRAY DIAGNOSTIC SYSTEM

[75] Inventors: Peter R. Teare, Westborough; William J. Hanson, Bolton; Matthijs Smits, Brookline, all of Mass.

[73] Assignee: Liberty Mutual, Boston, Mass.

[21] Appl. No.: 295,452

[22] Filed: Aug. 24, 1994

Related U.S. Application Data

[62] Division of Ser. No. 33,849, Mar. 19, 1993, Pat. No. 5,341,813.

[51] Int. Cl.$^6$ ............................................. A61B 5/04
[52] U.S. Cl. ................................................. 128/733
[58] Field of Search ................ 128/733, 774, 782, 905

[56] References Cited

U.S. PATENT DOCUMENTS

| | | | |
|---|---|---|---|
| 4,170,225 | 10/1979 | Criglar et al. | 128/733 |
| 5,085,225 | 2/1992 | DeLuca et al. | 128/733 |
| 5,085,226 | 2/1992 | DeLuca et al. | 128/733 |
| 5,086,779 | 2/1992 | DeLuca et al. | 128/733 |
| 5,233,999 | 8/1993 | Dellacorna et al. | 128/733 |
| 5,318,039 | 6/1994 | Kadefors et al. | 128/733 |

*Primary Examiner*—Max Hindenburg
*Attorney, Agent, or Firm*—Wolf, Greenfield & Sacks

[57] ABSTRACT

An apparatus for testing a muscle of a patient who is fitted with a myoelectric prosthetic device. The apparatus has an array of electrodes for testing the muscle over a wide area during a short period of time. The electric signals from the contraction are amplified, filtered, and converted to a digital signal. The digital signals are sent to a computer which causes a display to show one or more of the signals. A prosthetist uses the results to determine how to place the electrode in the device.

26 Claims, 10 Drawing Sheets

PROSTHETICS ELECTRODE ARRAY DIAGNOSTIC SYSTEM

This application is a division of application Ser. No. 08/033,849 filed Mar. 19, 1993, issued as U.S. Pat. No. 5,341,813 on Aug. 30, 1994.

FIELD OF THE INVENTION

This invention relates to an apparatus for testing and training patients to use myoelectrically controlled prosthetic devices.

BACKGROUND OF THE INVENTION

In a myoelectrically controlled prosthetic device, a motor controls the device in response to electrical signals from a muscle when the muscle contracts. The signals are received from an electrode or an electrode pair which is positioned on the skin surface adjacent the muscle. Myoelectric control is common in prosthetic arms, but can be used for other prosthetic devices.

To fit a patient with a myoelectric prosthetic device, a prosthetist or therapist tests the patient to determine the best place on the muscle to position the myoelectrode which may be an electrode pair. Generally, the optimal position is one where the myoelectric signal is strong in response to a contraction. For people with an intact muscle, the locations for a strong response are predictable. But for patients who are missing a portion of a limb, whether due to accident or birth defect, it is not uncommon that the remaining muscle remnant will not be otherwise intact and will not respond in the same manner as a muscle on a person with an intact limb.

Typically, a prosthetist uses a trial and error approach to determine the optimal position of an electrode pair. The prosthetist moves a single electronic probe over different portions of the muscle and requests that the patient contract the muscle each time the probe is positioned at a new location. As the prosthetist moves the electrodes to different locations in this manner, the prosthetist tries to locate the position in which the strongest signals are received. The resulting signals from separate contractions are inconsistent, however, because the effort expended by the patient is itself inconsistent from one contraction to another. Moreover, a patient may fatigue quickly when using a muscle that has remained dormant for several months. Consequently, the comparisons between locations are not based on identical conditions.

It would be desirable for a prosthetist to be able to simultaneously test locations on the muscle at the same time over a range of locations, and to compare the responses.

The patient should be trained to use the prosthetic device. For an amputee, the muscle contractions utilized to perform different tasks are not necessarily the same, natural contractions that the patient would have been using to perform those tasks prior to amputation. Accordingly, it would be desirable to have a system for assisting in training patients with new prosthetic devices.

SUMMARY OF THE INVENTION

It is an object of the present invention to provide an apparatus and method for a prosthetist to test different parts of a muscle under similar conditions at the same time.

It is another object of the present invention to provide a easy-to-use diagnostic system and method for measuring myoelectric signals in a short period of time over a wide muscle area.

It is yet another object of the present invention to provide an apparatus and method for training a patient to use a prosthetic device and for exercising the patient.

It is still another object of the present invention to provide a prosthetist with a portable device which can be used for testing and/or training.

These and other objects and advantages are addressed by a method for determining where to position a myoelectrode on a first muscle of a patient, where the myoelectrode is coupled to a research device or to a myoelectric prosthetic device. The method comprising the steps of positioning a plurality of electrodes over the surface of the first muscle; receiving input signals from the electrodes; providing output signals from the sampled electrodes; displaying the output signals; and determining where to position the myoelectrode on the first muscle based on the displayed output signals. These steps are generally performed by contracting, by the patient, the first muscle, and sampling at least some of the input signals during the contraction of the first muscle.

In preferred embodiments, the myoelectrode comprises an electrode pair, and an array of electrodes which form a plurality of electrode pairs is positioned over the muscle. Each of the electrode pairs has two electrodes which are spaced a distance which is about the same as a distance between the electrodes of the myoelectrode. This method can be repeated for a second muscle, so that two muscles which are used are both tested. Preferably, each electrode or electrode pair is sampled many times during a single contraction, and an average is determined of a number of samples for each electrode or electrode pair. The step of displaying comprising displaying the average for a plurality of electrodes simultaneously.

This method allows a prosthetist or therapist to determine a site for placing a myoelectrode for a prosthetic device, or a research electrode for experimentation. The method can be repeated for two muscles if the prosthetic device has two myoelectrodes for different muscles. The display provides meaningful indications for the prosthetist to compare the response from different sites during a single muscle contraction.

The invention also features an apparatus for detecting myoelectric signals from a muscle. The muscle is expected to be an electrode pair which is to be coupled to the muscle. The apparatus comprises a plurality of electrode pairs arranged in an array, so that the distance between the electrodes in each electrode pair about the same as the distance between the electrodes in the electrode pair of the device. Circuitry is coupled to the electrode pairs for sampling signals from a plurality of the electrode pairs during a muscle contraction and for providing output signals for each electrode pair during the contraction. Output signals are displayed for a plurality of the electrode pairs at the same time.

Preferably, the electrode pairs are mounted on a band which can be wrapped around the muscle. The band has a rigid mounting device which allows flexibility in a transverse direction and maintains the distance between electrodes in an electrode pair in a longitudinal direction. The circuitry preferably comprises a filtering circuitry and amplifying circuitry for the electrode pairs. This circuitry can be mounted on the band or in a separate box. The amplified and filtered signals can be coupled to one or more selectors. Preferably, the filtering circuitry attenuates frequencies above 350 hz and frequencies below 100 hz. If coupled to more than one selector, some electrodes are coupled to one selector, and other electrodes are coupled to another selector. The circuitry may comprise, for each electrode pair, amplifying circuitry, filtering circuitry, and an RMS to DC converter, and further comprise a selector coupled to at least some of the RMS to DC converters. With this circuitry, the averaging is performed in the converter, so sampling can be done quickly.

The apparatus preferably further comprises a means for selecting a display mode from among a plurality of modes. The modes may including a first mode for displaying an average over time for each electrode pair, and a second mode for displaying each sample for each electrode pair, so that all samples for each electrode pair are visible.

The apparatus provides a prosthetist or therapist with the ability to test a number of muscle sites at the same time, and to display the output from the test. The circuitry can quickly sample a number of sites many times to provide a meaningful comparison between sites during a single contraction. The device can be made portable with a lap top or hand-held computer, and with battery powered circuitry.

The invention also features a method for training a patient to use a myoelectric prosthetic device which has a myoelectrode for each of two muscles, each of which are used to control the device. The method comprises the steps of positioning a first myoelectrode on a first muscle, and positioning a second myoelectrode on a second muscle. The patient contracts one of the first and second muscles. Signals from each muscle are displayed while the patient contracts the one of the first and second muscles. In response to the displayed signals, it can be determined whether the patient should modify the contracting to improve use of the device.

In preferred embodiments, the step of displaying comprises displaying a difference signal which represents the difference in contraction between the first and second muscle when one of the first and second muscles is contracted, and an indication of expected angular motion of the device. The step of determining comprises determining that the patient needs to contract the muscles differently in response to a determination that the difference signal is too low.

This method provides a method for training a patient how to use a myoelectric prosthetic device, by teaching how to contract one muscle without contracting another. The difference signal is a visible indicator of the relative contraction in the two muscles.

BRIEF DESCRIPTION OF THE DRAWINGS

Other features and advantages will be apparent from the description of the preferred embodiments, the claims, and the following drawings in which:

DESCRIPTION OF THE PREFERRED EMBODIMENTS

Figure 1:
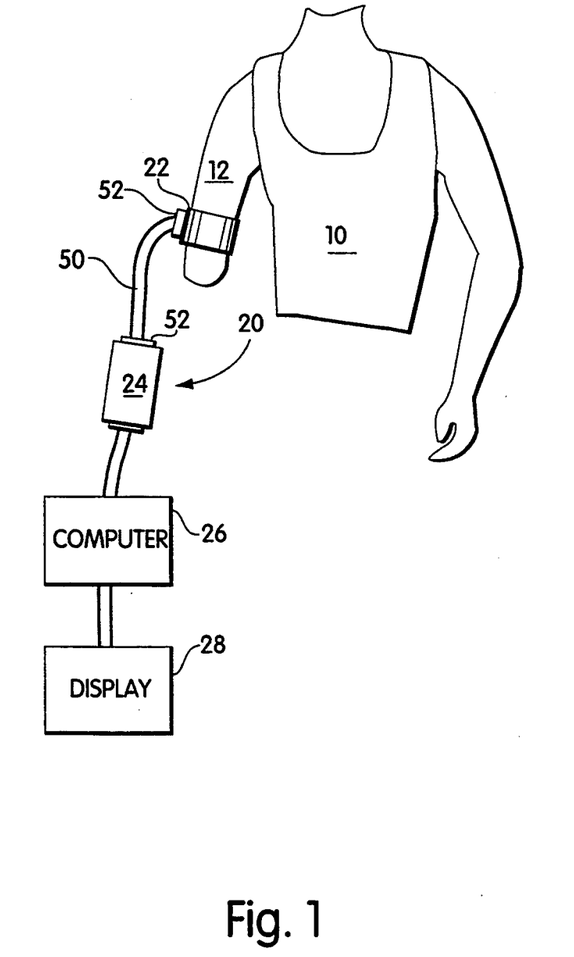
FIG. 1 is a pictorial block diagram of an embodiment of the present invention.

A patient and a diagnostic system 20 according to an embodiment of the present invention are illustrated in FIG. 1. The patient 10 has an arm 12 which is severed from above the elbow. The patient is being fitted with a prosthetic device, such as the Boston Elbow, which is available from Liberty Mutual Insurance Co., of Boston, Mass. The Boston Elbow has two myoelectrodes, each having an electrode pair, i.e. two electrical contacts spaced a distance apart. One myoelectrode receives myoelectric signals from the bicep for elbow flexion, and the other receives myoelectric signals from the tricep for elbow extension.

A prosthetist uses the diagnostic system 20 to determine the optimal position on the arm for placing each myoelectrode. The system has a myoelectric array 22 which is positioned against a portion of the arm 12 over the muscle site. Optionally, conductive cream is first applied to the test area of the arm. The array 22 has electrode pairs which receive electrical signals from the arm. These signals are amplified, filtered, and digitized by circuitry 24 which in turn provides conditioned signals to a computer 26. The computer, which may be a full size computer or a more portable hand-held or lap top, provides absolute and comparative measures of the conditioned signals which are displayed on a display 28.

Figure 2:
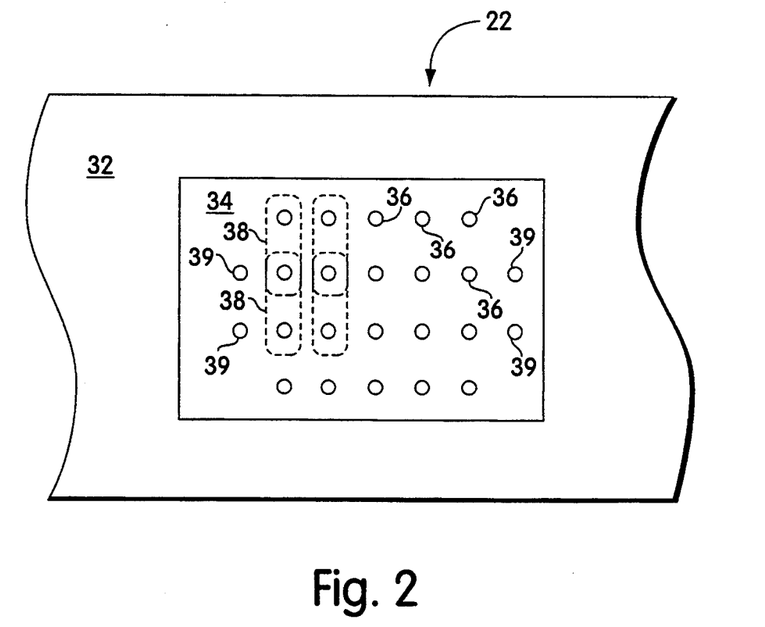
FIGS. 2 and 3 are plan views of opposite sides of a myoelectric array accordingly to the present invention.
Figure 3:
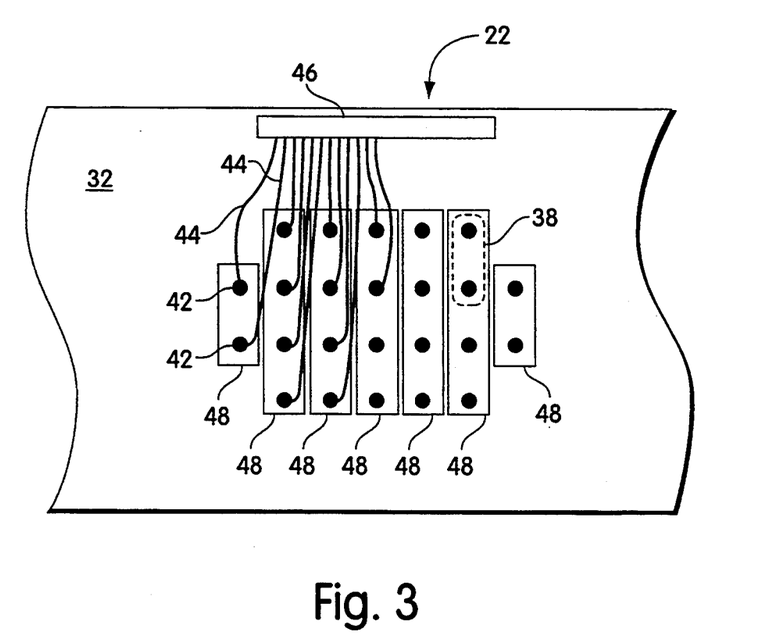

FIGS. 2 and 3 show the front and back sides, respectively, of the array 22, which is preferably mounted on an elastic band 32. The front is the side which is placed in face-to-face contact with the patient's arm. A component, such as Velcro strips (not shown), holds the two ends of the band together when the band is wrapped around the patient's arm.

Referring to FIG. 2, the front side has a plastic panel 34 which holds a number of electrodes 36, which are preferably stainless steel. Twenty separate electrodes are shown in a five-by-four array. Pairwise, these electrodes constitute fifteen electrode pairs 38. Each pair consists of two adjacent electrodes in the longitudinal direction, i.e., the direction along the direction of the array with four electrodes. Thus there are three electrode pairs in each of five longitudinal columns. As can be observed from FIG. 2, the two middle electrodes in each column are part of two separate electrode pairs. At each end of the array are two ground electrodes 39.

Referring to FIG. 3, each electrode 36 (FIG. 2) has a corresponding contact 42 and a wire 44. All the wires 44 from all the contacts 42 are coupled to an output port 46. The contacts 42 are arranged on plastic strips 48 which extend in a longitudinal direction. When the elastic band 32 is mounted on a patient's arm, the strips 48 can separate when the band stretches in the transverse direction. The distance in the longitudinal direction between the electrodes in each electrode pair 38 is constant. This distance should correspond to the distance between electrodes in an electrode pair of the prosthetic device which is to be mounted. Accordingly, if the Boston Elbow is used, the distance between the electrodes in an electrode pair 38 should be the same distance as the distance between the electrodes in the electrode pairs which are used for the Boston Elbow. The distance between electrodes in the Boston Elbow is similar to the distance between electrodes in other devices. Another array should be used if a prosthetic device with different electrode spacing is to be used.

Referring again to FIG. 1, circuitry 24 is coupled to the array 22 through a bus 50. At each end of the bus is a connector 52 which mates with a port, such as port 46 (FIG. 3). The connector 52 should provide for a secure connection, but also be fairly easy to disconnect.

Figure 4:
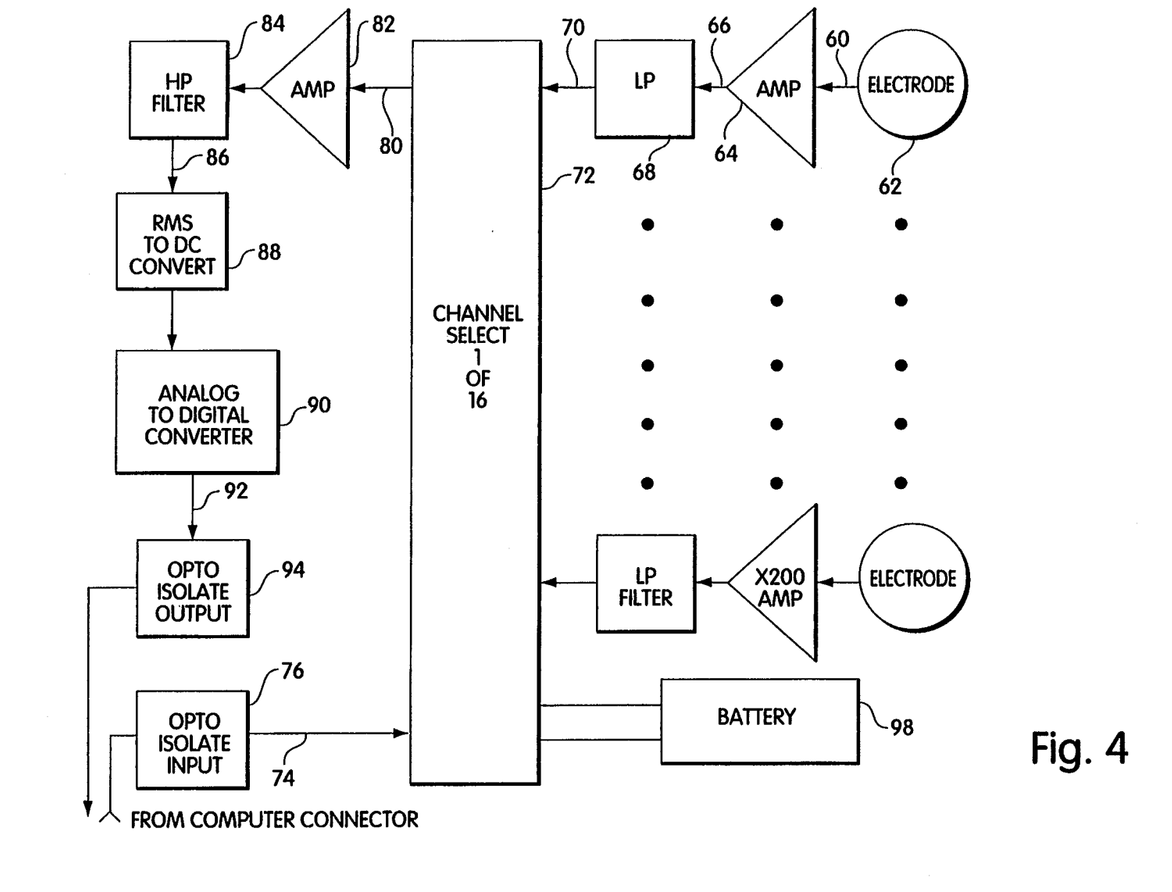
FIG. 4 is a block diagram of circuitry a first embodiment of the present invention.
Figure 5:
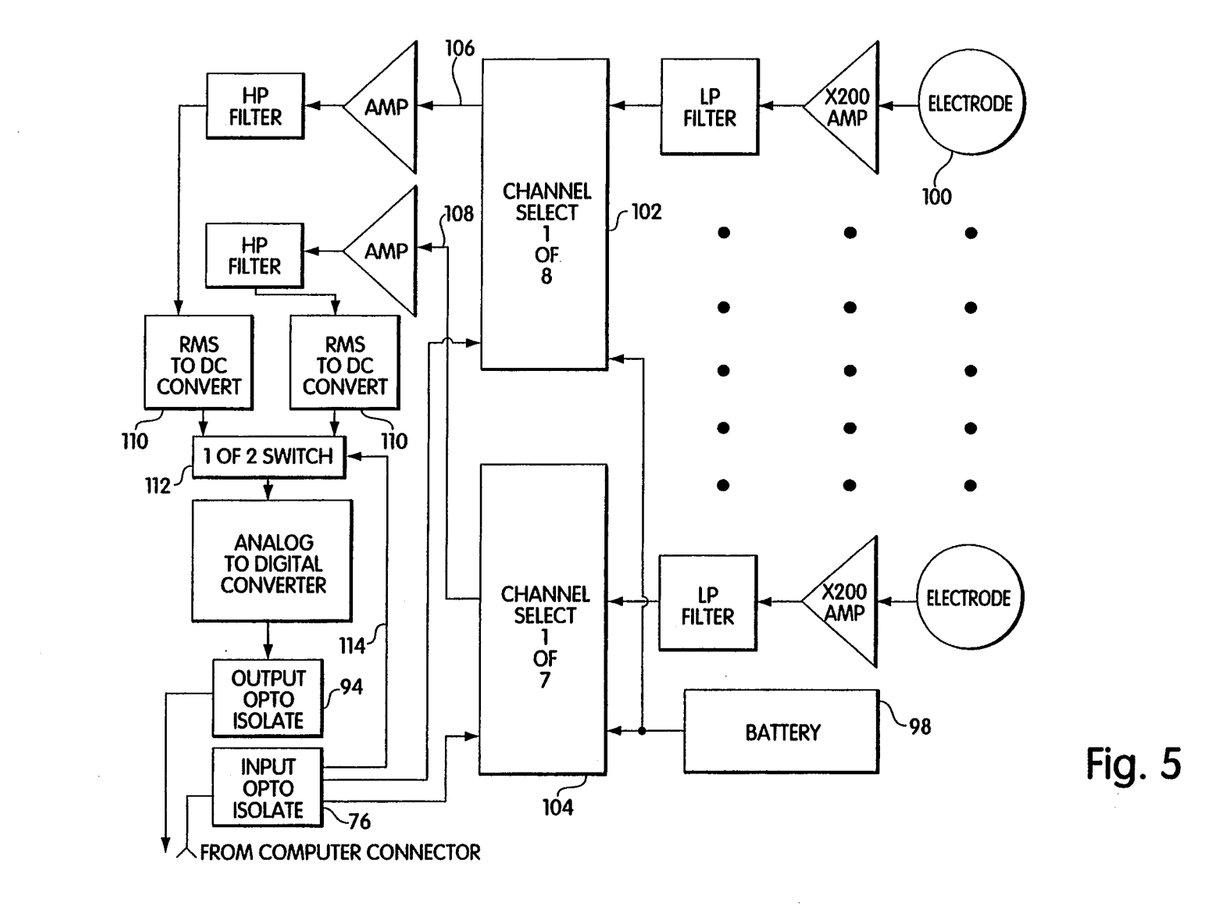
FIG. 5 is a block diagram of circuitry according to a second embodiment of the present invention.

FIGS. 4 and 5 are block diagrams of circuity of two possible embodiments of the invention. Referring to FIG. 4, in the first embodiment, a signal 60 from each electrode pair 62 is amplified with a gain of 200 in amplifier 64. The amplified signal 66 is passed to a low pass filter 68 which causes frequencies above about 350 hz to attenuate. Each of the filtered signals 70 is provided to a channel selector which receives a signal 74 from the computer 26 (FIG. 1) through optical isolating input 76. The computer directs the selector 72 to output a signal 80 which is a selected one of the filtered signals 70. The selected signal 80 is amplified in amplifier 82 and passed to high pass filter 84 which attenuates frequencies above about 100 hz. The filtered signal 86 is converted to DC by converter 88, and is converted to a digital signal in analog-to-digital convertor 90. The digitized signal 92 is provided to the computer through optical isolation output unit 94.

A battery 98 powers the components which are separated by optical isolation units 76 and 94. These isolating units are utilized to satisfy regulations requiring electrical isolation between the patient and the computer when tests are performed on human subjects. The optical units provide complete, safe isolation if the computer is powered from an electrical outlet. If a lap top is used, the system can be easily transported and set up, without a power outlet.

The computer can monitor one or more specific electrodes, or it may sample all of the electrodes in succession at the rate of about 1000 samples/second. When sampling, an electrical spike appears before the signal settles to a more steady level which can be used by the prosthetist. The settling time is about 10% of the total sample time. For the remaining 90% of the sample time, the signal is averaged to produce a value for that electrode pair. The settling time may be reduced by further amplifying the signal. At 1000 samples/second, each sample takes 1 msec, and every channel is sampled for at least 100 msec. Since a muscle contraction can be held for about 3-5 seconds, one contraction can be sampled by each channel many times. The prosthetist can measure and compare the signals at different locations for a single muscle contraction, thus avoiding the problem discussed above of using a different contraction for each tested site. Of course, a prosthetist may wish to obtain readings for several muscle contractions. For each contraction, the prosthetist will obtain signals for all fifteen electrode pairs almost simultaneously.

Referring to FIG. 5, a second embodiment is shown in which signals from electrode pairs 100 are similarly amplified and filtered but are provided to one of two computer-controlled channel selectors 102, 104. The output signals 106, 108 from the channel selectors 102, 104 are similarly amplified, filtered, and converted to an analog DC signal in converters 110. The output from each converter 110 is provided to a switch 112 which is controlled by a signal 114 from the computer. By using the two channel selectors 102, 104 and the switch 112, the computer can sample a signal from one electrode pair, while another pair is settling, thus reducing the time period between each sample. This ability is useful because a prosthetist would prefer to compare signals at different points as close to simultaneously as possible, to give a more accurate comparison. More selectors and switches can be added if desired.

Figure 11:
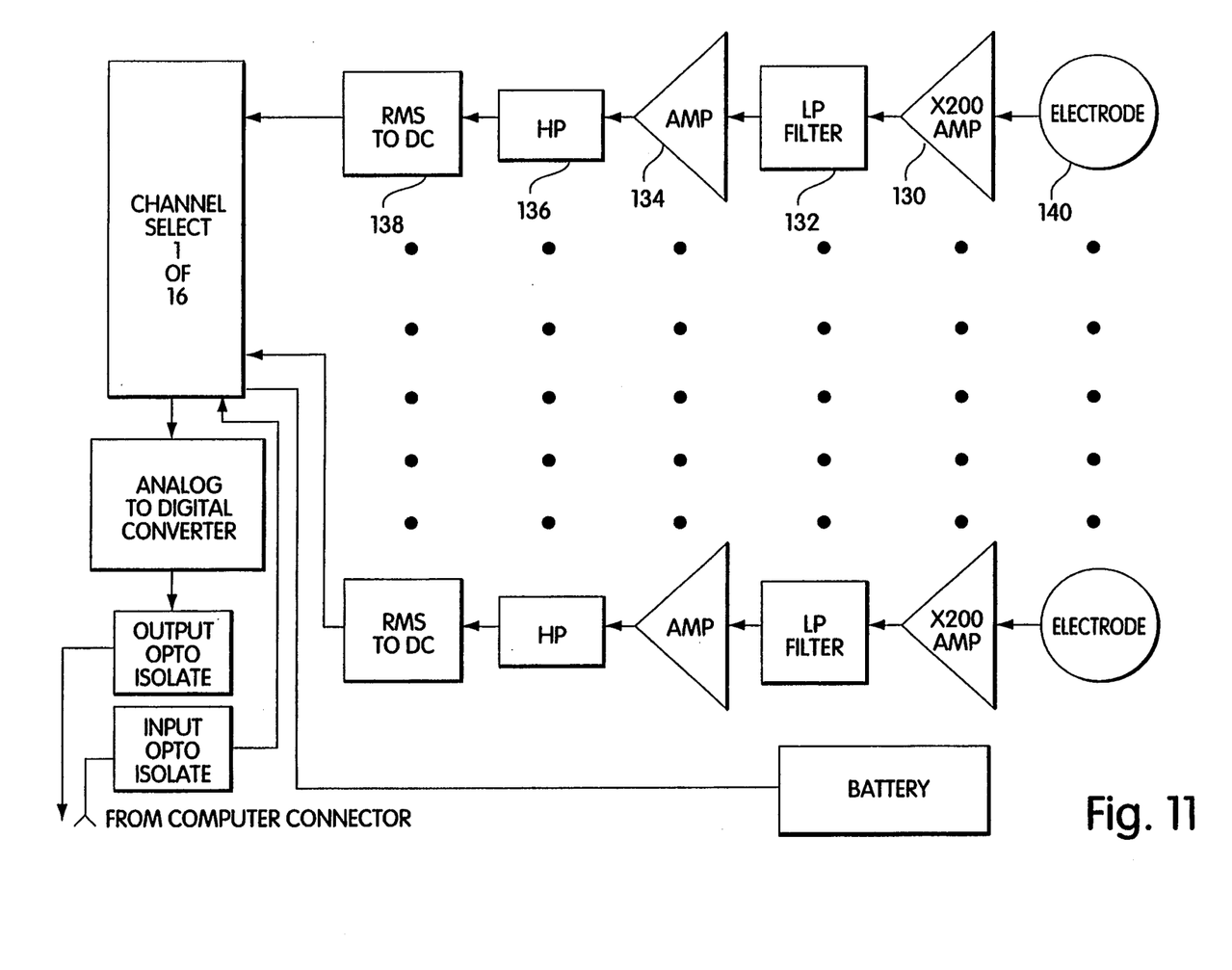
FIG. 11 is a block diagram of the circuitry according to a third embodiment of the present invention.

Referring to FIG. 11, in another embodiment of the circuitry according to the present invention, an amplifier 130, a low-pass filter 132, another amplifier 134, a high-pass filter 136, and an RMS to DC converter 138 are provided for each electrode pair 140, prior to the switch or selector. The converter 138 performs the averaging by holding the previous signals for a certain time, e.g., 100 msec. The battery, channel selector, A/D converter, and optical isolating elements are similar to those in FIG. 4. With this circuitry, the computer does not need to perform the averaging calculations, and thus less computing power is required. There are no limitations due to settling time or scan time. A scan of the entire array of 15 electrode pairs could be performed in about 15 msec.

Figure 6:
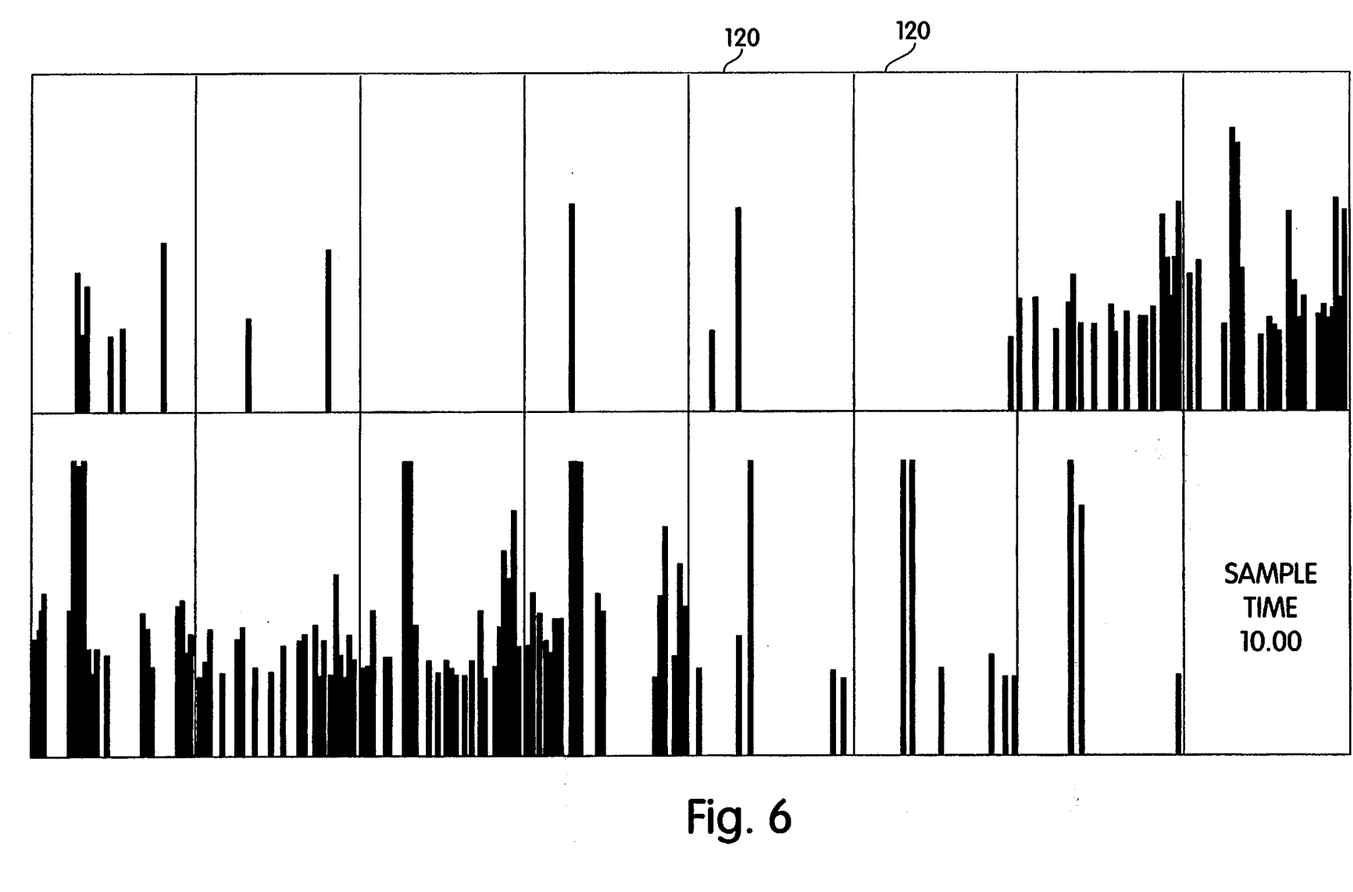
FIGS. 6–10 are examples of displays which can be generated according to the present invention.

FIGS. 6-10 demonstrate different display modes which can be used by a prosthetist. Referring to FIG. 6, the fifteen channel display has fifteen windows 120, each corresponding to one of the fifteen channels (i.e., fifteen electrode pairs). A series of bars appears within each channel, each bar representing the relative magnitude of a sample for that channel. Where the bars are wide, several successive samples had roughly the same output level. In each window, the bars represent a percentage of maximum output over time. A maximum of 100% represents the maximum signal which is recorded by the prosthetic device to be fitted. For example, if the maximum input to the device is 1.0 mv, and the gain is 6000, a 100% reading represents 6.0 v of output. Each sample causes a new bar to be added to the next window. The bars are added successively to a next window, so a bar appears in the first window, then in the second window, then in the third, etc., and the cycle is repeated. Since the system can perform at least 1000 samples each second, a single bar representing 50 samples is provided for all the channels in about 150 msec. Because of the speed of sampling, the display seems to provide an advancing graph in each window simultaneously. In FIG. 6, the total sampling time is about 10.0 seconds, which means each channel is sampled about 66 times.

Figure 7:
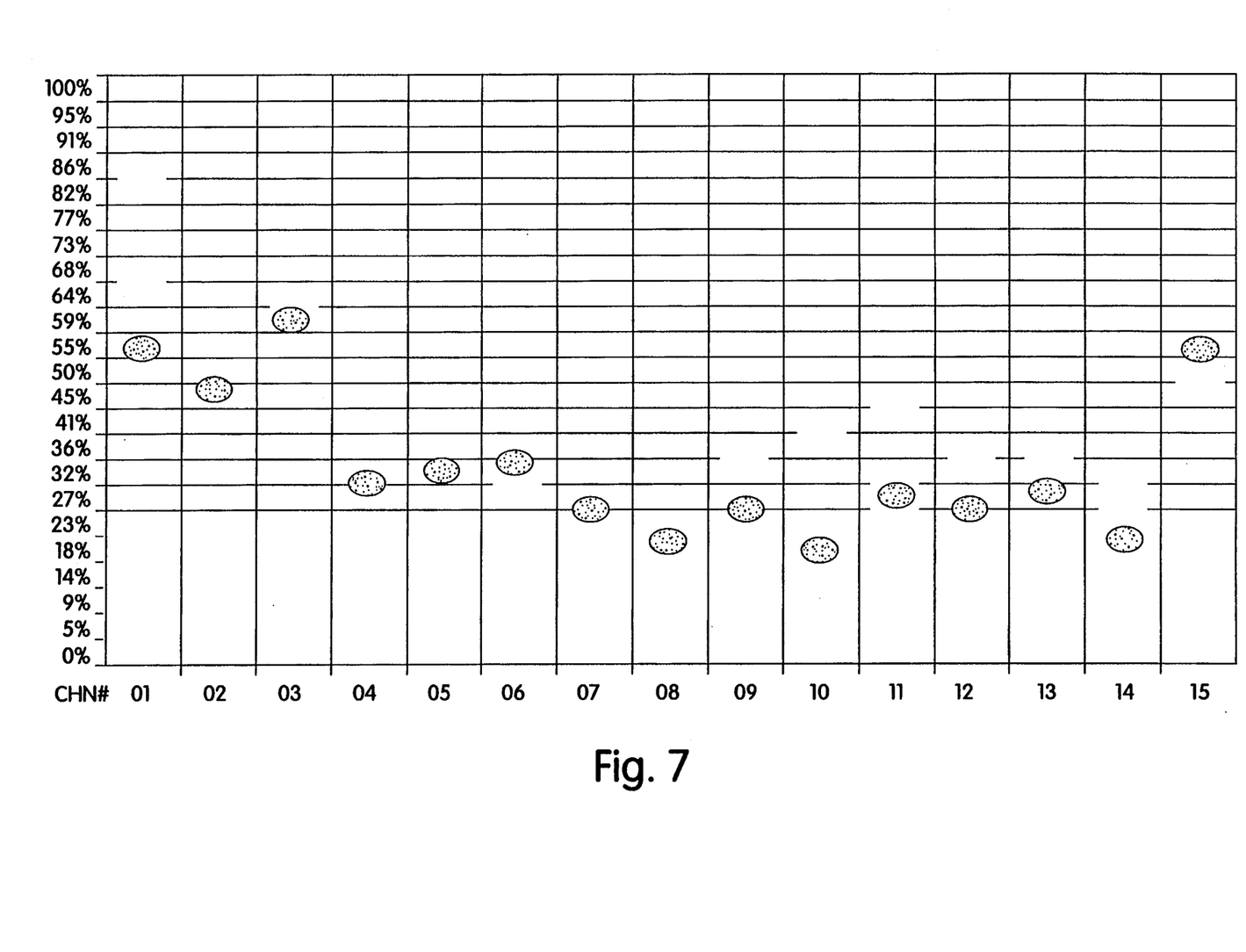

Referring to FIG. 7, a different type of display mode showing a fifteen channel ball display is illustrated. Each ball represents a percentage of the signal for each channel averaged over a period of time. By averaging, the balls can hold their position, so the value can be assessed. For a number of the channels, there is a broken line in the graph which indicates a previous high value.

Figure 8:
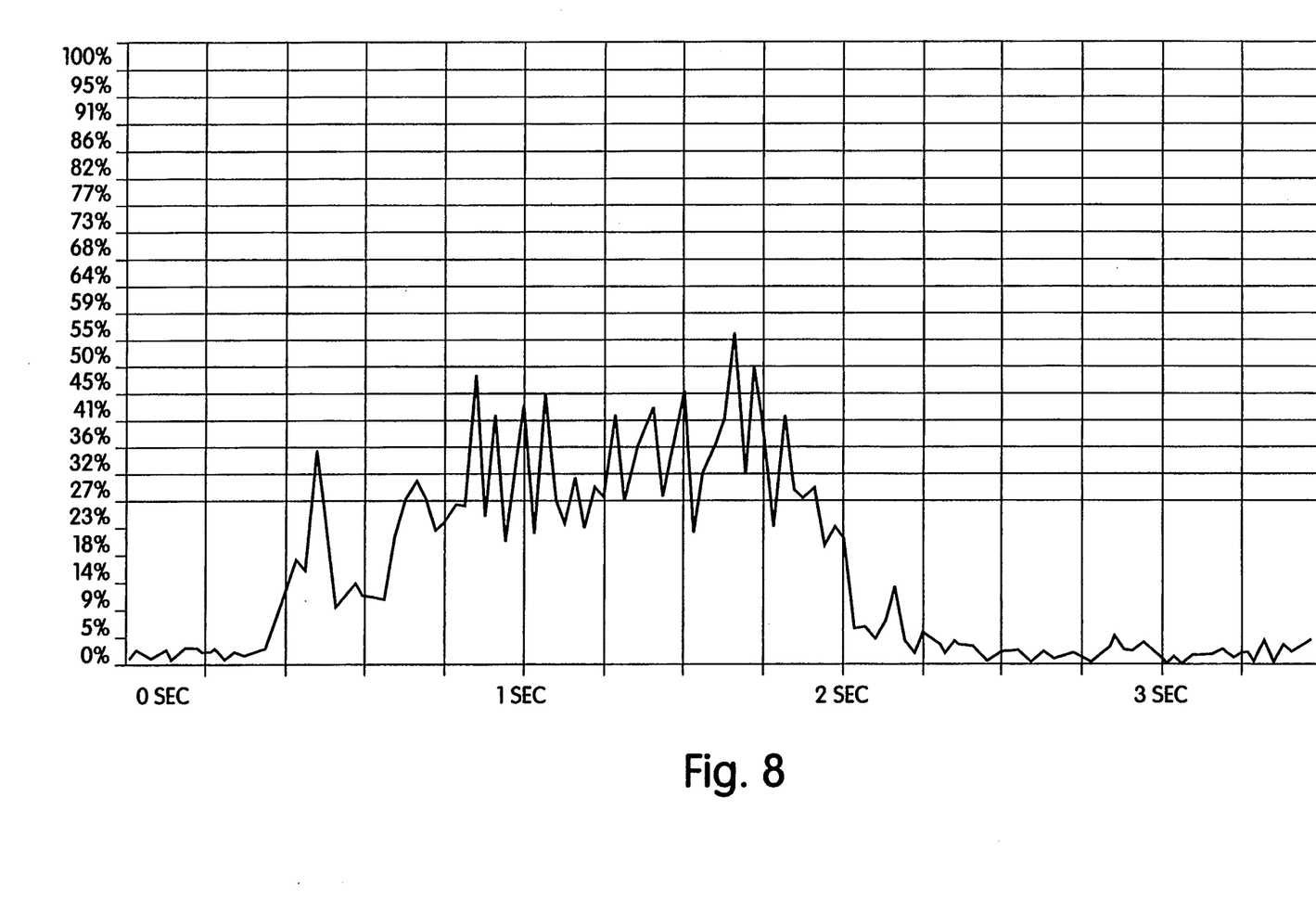

Referring to FIG. 8, the display shows the output signal over a period of time for a selected channel. The channel can be selected and changed by the user.

Figure 9:
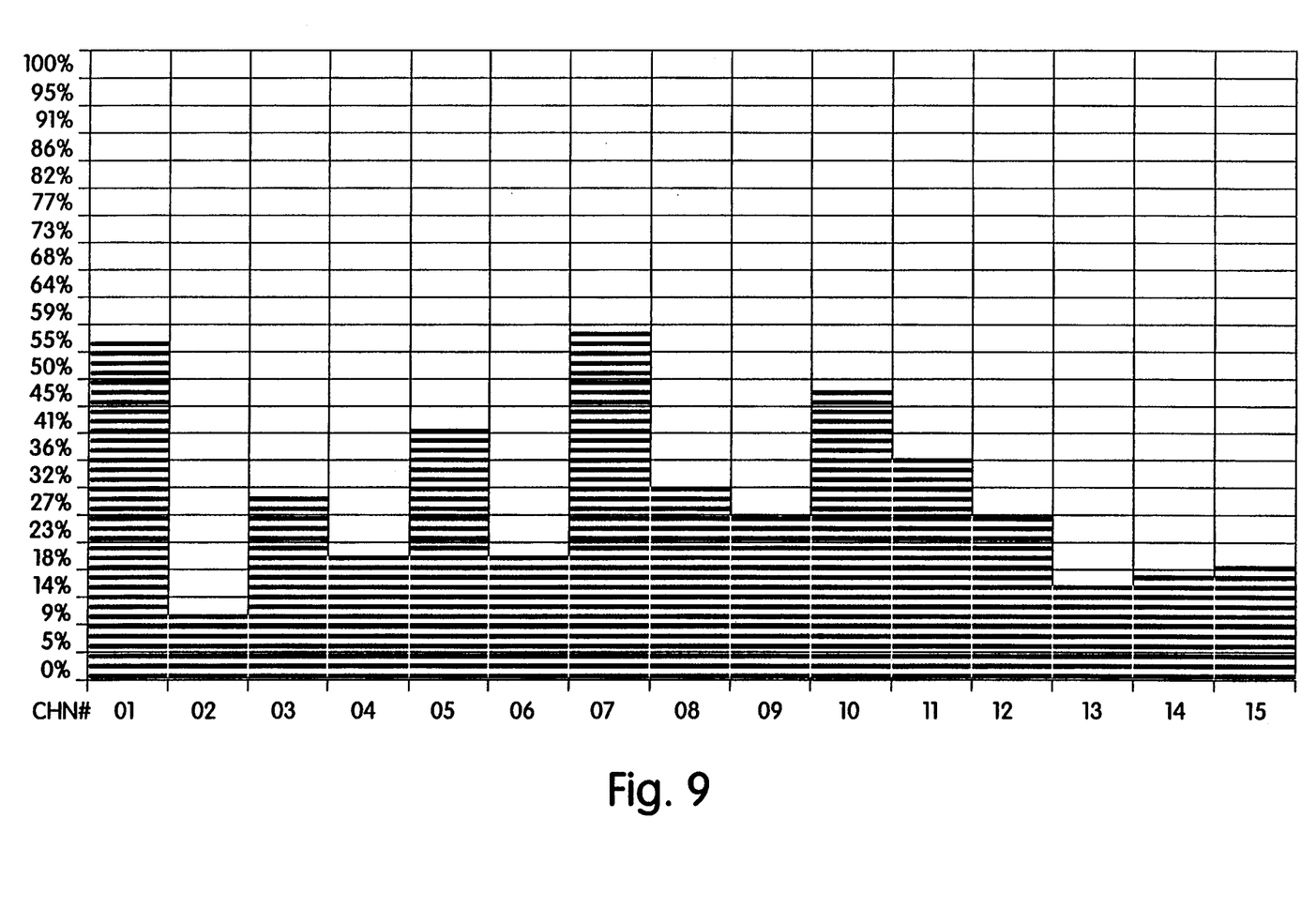

FIG. 9 shows a bar graph display which has values for each channel. In this display, one channel can be observed during a contraction while other channels are held at a previous value.

The prosthetist uses these displays and data to determine how to position a single electrode pair for a myoelectric prosthetic device. The prosthetist can rely on the data and his or her experience in working with patients to determine the optimal position of the electrodes. Typically, the prosthetist is interested in the locations which have the maximum peaks during contraction over the muscle's range of motion, and lowest base line values when not contracting. To position an elbow device, the prosthetist may perform this test for the bicep and tricep, or on some other muscles if these cannot be used. When the test is completed and the array is removed from the patient's arm, non-harmful, temporary indentations are left in the patient's arm by the electrodes. These indentations make it fairly easy to visually identify where the electrodes were positioned after the array is removed.

The present invention along with the display can also be used to assist in training a patient for a new prosthetic device or with a recently acquired prosthetic device. For a prosthetic elbow, training is performed with two electrode pairs which are positioned at two muscles, preferably the bicep and the tricep. Since one of these muscles is for flexion, and the other is for extension, each counteracts the other. Preferably, the patient contracts each muscle separately, while contracting the other as little as possible to get a better response from the intended contraction.

Figure 10:
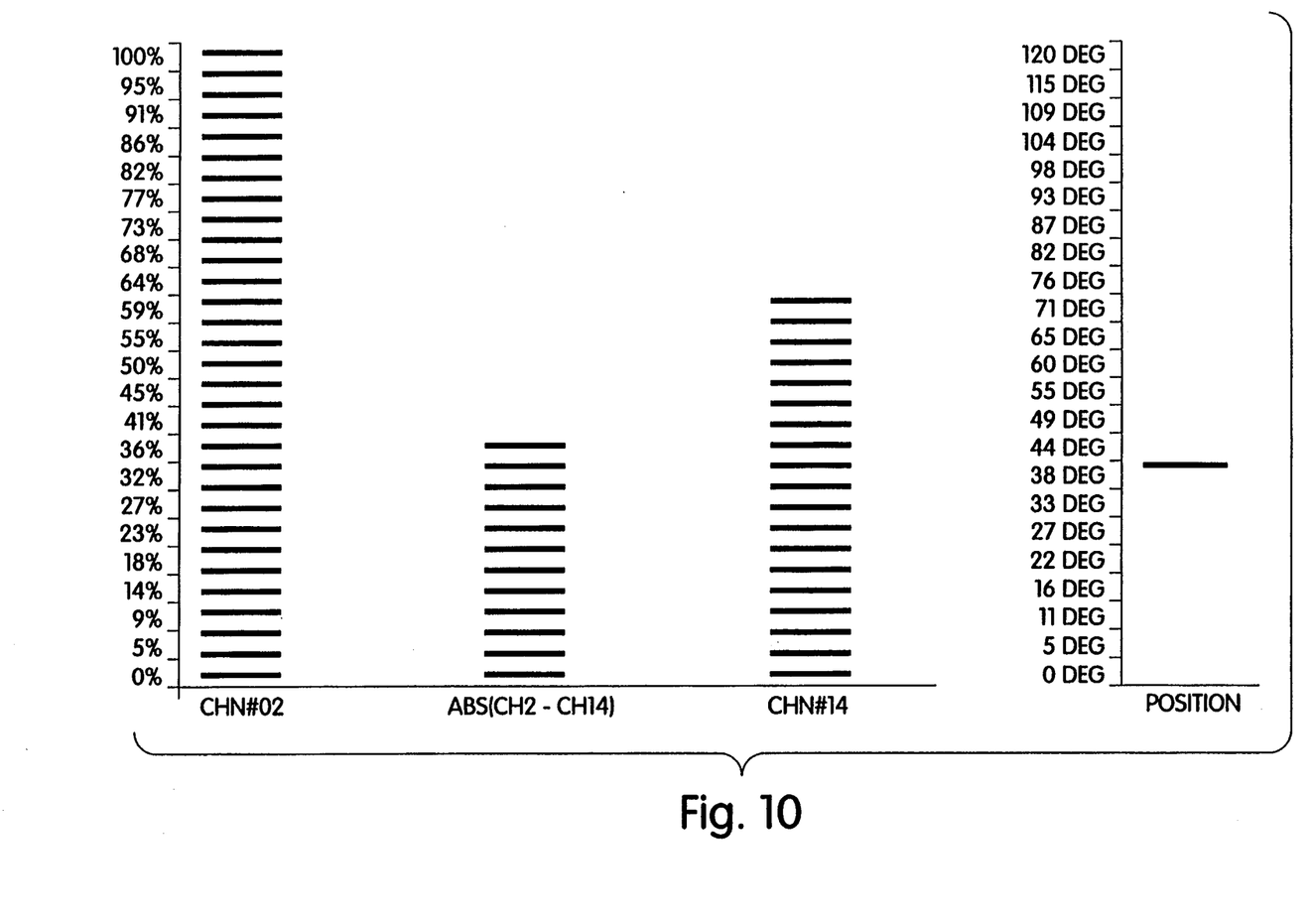

An example of the training aspect is shown in FIG. 10. The display has two channels in the first and third columns, one for each muscle, e.g., bicep and tricep. In the second column a difference signal between the two channels is provided. The fourth column shows the position of the arm as an angle relative to a horizontally extended position. During training, the patient learns to control the muscles to work independently. It is desirable for the patient to cause the bicep to contract for curling the elbow without contracting the tricep which opposes the bicep. Accordingly, the patient is taught to practice keeping the difference level high while working through the range of motion as shown in the fourth column.

Other embodiments are within the following claims. For example, some of the circuitry can be positioned on the band with the myoelectric array, and other indicators could be provided on the band. For instance, LED's could be positioned on the outside of the band for each electrode pair to indicate which pair had the maximum value at a given time. Alternatively, more of the circuitry, such as that shown in FIGS. 4, 5, and 11, could be mounted on the band itself. The system could also be used to determine a location with optimal response for other research purposes, rather than for coupling a myoelectric prosthetic device. While the examples have mainly addressed a prosthetic elbow, the device could also be used for patient's seeking a forearm, hand, leg, or some other prosthetic devices. In addition, the array could be mounted on a rigid band, and not necessarily on an elastic band.

Having thus described a few particular embodiments of the invention, various alterations, modifications and improvements will readily occur to those skilled in the art. Such alterations, modifications and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. An apparatus for detecting myoelectric signals from a muscle which is to be coupled to a myoelectric prosthetic device, said device having a device electrode pair which is coupled to the muscle, the apparatus comprising:

a plurality of electrode pairs arranged in an array, wherein the distance between the electrodes in each electrode pair is the same as the distance between the electrodes in the device electrode pair, wherein the electrode pairs are sufficient in number and are sufficiently spaced apart to cover a wide area of the muscle so that the muscle can be tested without it being necessary to reposition the electrode pairs;

circuitry coupled to the electrode pairs for sampling signals from a plurality of the electrode pairs during a muscle contraction and for providing output signals for each electrode pair during the contraction; and a display for displaying the output signals for a plurality of the electrode pairs at the same time.

2. The apparatus of claim 1 wherein the electrode pairs are mounted on a band for wrapping around the muscle, the band having flexibility in a transverse direction and being a support mechanism for maintaining the distance between electrodes in an electrode pair fixed in a longitudinal direction.

3. The apparatus of claim 2 wherein the circuitry comprises a filter and an amplifier for each electrode pair, wherein the filters and amplifiers are each mounted on the band.

4. The apparatus of claim 1 wherein the circuitry comprises:

amplifying and filtering circuitry coupled to each electrode pair for providing an amplified, filtered input signal; and a selector coupled to each electrode for receiving all of the amplified, filtered input signals.

5. The apparatus of claim 1 wherein the circuitry comprises:

amplifying and filtering circuitry coupled to each electrode pair for providing an amplified, filtered input signal; and a first selector coupled to some, but not all, of the electrode pairs for receiving some of the amplified, filtered input signals; and a second selector coupled to some, but not all, of the electrode pairs for receiving some of the amplified, filtered input signals, the first and second selectors being coupled to different electrode pairs.

6. The apparatus of claim 1 wherein the circuitry comprises, for each electrode pair:

amplifying circuitry,
   filtering circuitry, and
   an RMS to DC converter;
   said circuitry further comprising:
      a selector coupled to at least some of the RMS to DC converters.

7. The apparatus of claim 7 further comprising:

means for selecting a display mode from among a plurality of modes, the modes including:
      a first mode for displaying an average over time for each electrode pair, and
      a second mode for displaying each sample for each electrode pair, so that all samples for each electrode pair are visible.

8. The apparatus of claim 1 further comprising a portable computer, and wherein the circuitry is battery powered, the apparatus being portable.

9. The apparatus of claim 1 wherein the circuitry comprises filtering circuitry which attenuates frequencies above 350 hz and frequencies below 100 hz.

10. The apparatus of claim 1, wherein the electrode pairs consist of individual electrodes arranged in a two dimensional array.

11. The apparatus of claim 10, wherein the two dimensional array includes a portion having about 4 rows and 5 columns of electrodes.

12. The apparatus of claim 10 wherein the two-dimensional array includes a group of electrodes in an $n \times m$ array, forming $(n-1) \times m$ electrode pairs.

13. The apparatus of claim 1 wherein the electrodes are arranged in a plurality of longitudinal columns.

14. The apparatus of claim 12, wherein the stored signals include peak values of myolectric activity prior to the second contraction, and wherein the output signals include relative magnitudes of myoelectric activity during the second contraction in real time.

15. An apparatus comprising:
a first electrode pair for positioning over a first muscle;
a second electrode pair for positioning over a second muscle;
circuitry coupled to the first and second electrode pairs for sampling signals from the first and second electrode pairs during muscle contractions and for providing respective first and second output signals, the circuitry including means for determining a difference between the first and second output signals and for providing a difference signal, the difference signal indicating a simultaneous difference in the myoelectric signals for the first and second muscles; and
a display for displaying an output signal indicating the difference in the myoelectric signals for the first and second muscles.

16. The apparatus of claim 15, wherein the circuitry further includes means for determining an angle of angular movement when a muscle is contracted.

17. An apparatus for measuring myoelectric signals from a muscle of a person to determine an optimal position for positioning a myoelectrode for a prosthetic device, the apparatus comprising:
a plurality of electrode pairs positioned over the muscle of the person;
circuitry for receiving input signals from each of the electrode pairs during first and second muscle contractions and for providing respective output signals;
memory for storing magnitude signals derived from the output signals for the first muscle contraction; and
a display for displaying, at the same time, information derived from the stored magnitude signals from the first contraction and the output signals for the second contraction so that the first and second contractions can be compared.

18. The apparatus of claim 17, wherein the plurality of electrode pairs are positioned over a wide muscle area.

19. An apparatus for measuring myoelectric signals from a muscle of a person to determine an optimal position for a myoelectrode for a prosthetic device, the apparatus comprising:
a plurality of electrode pairs positioned over the muscle;
circuitry for receiving input signals indicative of myoelectric activity of the muscle from each of the electrode pairs when the person contracts the muscle, and for providing a signal indicating a relative magnitude of myoelectric activity over time; and
a display, coupled to the circuitry, for displaying, for at least one electrode pair, an output derived from the signal indicating the relative magnitude of myoelectric activity versus time.

20. The apparatus of claim 19, wherein the display simultaneously displays the output signals of all the electrode pairs as relative magnitudes of myoelectric activity versus time.

21. The apparatus of claim 19, further comprising means for selecting from among a plurality of display modes including a first mode for displaying a relative magnitude of myoelectric activity with respect to time for at least one electrode, and a second mode for displaying a relative magnitude of myoelectric activity in real time.

22. The apparatus of claim 19, wherein the display simultaneously displays the relative magnitudes of myoelectric activity versus time for a plurality of electrode pairs so that the relative magnitudes of myoelectric activity can be observed for each electrode pair at the same time.

23. The apparatus of claim 19, wherein there is a sufficient number of electrode pairs to cover a wide muscle area.

24. The apparatus of claim 23, wherein the electrode pairs are arranged in a two-dimensional array.

25. A portable apparatus for detecting myoelectric signals from a muscle to determine an optimal location to position a myoelectrode for a prosthetic device, the apparatus comprising:
a plurality of electrode pairs arranged in a two-dimensional array, wherein the electrode pairs are sufficient in number and are sufficiently spaced apart to cover a wide area of the muscle so that the muscle can be tested without it being necessary to repositioning the array of electrode pairs, the electrode pairs being mounted on a single, easily attachable and removable elastic band, the electrodes being oriented in columns which are in a fixed spaced relation in a longitudinal direction, and wherein the columns are flexibly arranged in a direction transverse to the longitudinal direction;
circuitry coupled to the electrode pairs for sampling signals from a plurality of the electrode pairs during a muscle contraction and for providing output signals for each electrode pair during the muscle contraction; and
a display for displaying output signals for a plurality of electrode pairs at the same time, the display providing a plurality of display modes for comparing relative magnitudes of the signals from the electrode pairs to determine a preferred location for attaching a myoelectrode of a prosthetic device, wherein the electrode pairs, circuitry, and display are combined in a portable kit.

26. The apparatus of claim 25 wherein the plurality of display modes includes:
a first display mode in which relative magnitudes of the signals are displayed in real time for all of the electrode pairs; and
a second display mode including a peak-hold display which has a maximum relative magnitude for a previous contraction and a relative magnitude in real time for each of the electrode pairs.

* * * * *